United States Patent [19]

Robel

[11] Patent Number: 4,973,595

[45] Date of Patent: Nov. 27, 1990

[54] COMPOSITION AND METHOD FOR INCREASING THE HATCHABILITY OF TURKEY EGGS

[75] Inventor: Edward J. Robel, Laurel, Md.

[73] Assignee: The United States of America as represented by the Secretary of Agriculture, Washington, D.C.

[21] Appl. No.: 362,992

[22] Filed: Jun. 8, 1989

[51] Int. Cl.$^5$ .................... A61K 31/44; A61K 31/65; A01K 45/00

[52] U.S. Cl. .................... 514/345; 514/154; 119/6.8

[58] Field of Search ............... 119/1; 514/154, 277, 514/345

[56] References Cited

U.S. PATENT DOCUMENTS

| | | | |
|---|---|---|---|
| 2,477,752 | 8/1949 | Kiss et al. | 119/1 |
| 3,966,922 | 6/1976 | Okamoto et al. | 514/154 |
| 4,040,388 | 8/1977 | Milles | 119/1 |

OTHER PUBLICATIONS

CA9186d: *B-Vitamin Deficiency in the Mature Turkey Hen*, T. M. Ferguson et al., date: 1961.

CA:2784:8, *Effect of Vitamin $B_6$ on Egg Production and Hatchability*, Cravens et al.

Edward J. Robel, "The Effect of Age of Breeder Hen on the Levels of Vitamins and Minerals in Turkey Eggs", Poult. Sci. 62: 1751–1756 (1983).

Edward J. Robel, "Comparison of Avidin and Biotin Levels in Eggs from Turkey Hens with High and Low Hatchability Records", Comp. Biochem. Physiol. 00B(0): 000–000 (1986).

E. J. Robel et al., "Increasing Hatchability of Turkey Eggs with Biotin Egg Injections", Poult. Sci. 66: 1429–1430 (1987).

*Primary Examiner*—Douglas W. Robinson
*Assistant Examiner*—Keven Weddington
*Attorney, Agent, or Firm*—M. Howard Silverstein; Curtis P. Ribando; John D. Fado

[57] ABSTRACT

The hatchability of fertile turkey eggs is increased by injection of the eggs with an effective amount of exogenous pyridoxine. The eggs are preferably injected between the outer and inner membranes following up to 25 days of incubation. Hatchability increases up to 5% have been observed.

4 Claims, No Drawings

COMPOSITION AND METHOD FOR INCREASING THE HATCHABILITY OF TURKEY EGGS

BACKGROUND OF THE INVENTION

1. Field of the Invention

This invention relates to a treatment to increase the hatchability of fertile domestic turkey eggs. In particular, the present invention relates to a composition and a method of injecting fertile turkey eggs with exogenous pyridoxine to enhance the hatchability thereof.

2. Description of the Prior Art

The national average hatch rate of turkey eggs is about 20% lower than that of chicken eggs. Many variables contribute to this low hatch record in turkeys, but it is well recognized in the turkey industry that one factor is a deficiency of vitamins in the diet of breeder turkey hens. To cure this deficiency, modern commercial diets are fortified with a variety of synthetic vitamins. However, the relationship between vitamins and hatchability in the turkey remains complex and unresolved. Preliminary investigations have revealed that pyridoxine drops to low levels in the egg with maternal age of the hen [Robel, Fed. Amer. Soc. Exp. Biol. Med. 41: 1129 (1982); Robel, Poult. Sci. 62: 1751-1756 (1983)]. Environmental stress and the presence of vitamin binding proteins may also be factors in pyridoxine deficiency.

Robel [Comp. Biochem. Physiol., B: Comp. Biochem. 84B: 265-267 (1987)] reported that, as a result of certain field stress factors, certain breeder turkey hens experience hormonal imbalance which causes significantly high levels of avidin to be deposited into the albumenous portion of the egg. Avidin, which is a glycoprotein secreted in the magnum region of the oviduct of the hen, is hormonally induced and binds with biotin, rendering the nutrient unavailable for use. During the initial stages of development, the embryos are not adversely affected by the high levels of avidin because the yolk, which is protected by the yolk sac, provides a sufficient supply of free biotin for normal development. Following the second quarter of incubation, approximately 15-16 days of incubation, the yolk sac ruptures, and the avidin-rich albumen passes progressively into the yolk. At this point, a biotin deficiency occurs within the eggs as the high concentration of avidin makes biotin unavailable to the embryo by forming an avidin-biotin complex.

Robel et al. [Poult. Sci. 66: 1429-1430 (1987)] found that by injecting the avidin-rich eggs with exogenous d-biotin in an inert liquid carrier after at least 23 days of incubation, the eggs were replenished with the supply of free biotin necessary for embryonic survival. The result was an increase in hatch rate up to 5%.

SUMMARY OF THE INVENTION

I have now surprisingly found that a similar increase in hatch rate is obtained when turkey eggs are injected with pyridoxine (vitamin $B_6$) during incubation. Unlike biotin, pyridoxine is not known to form a complex with avidin which would make the vitamin nutritionally unavailable. Therefore, the benefits of in ovo supplementation of pyridoxine are not predictable from the results observed for biotin.

In accordance with this discovery, it is an object of the invention to provide a method for increasing the amount of available pyridoxine in fertile turkey eggs, particularly in eggs which are pyridoxine-deficient as a result of aging hens or in eggs of flocks which have not responded sufficiently to dietary supplementation of pyridoxine.

It is also an object of the invention to provide a pyridoxine composition useful to increase the batch rate of fertile turkey eggs.

Another object of this invention is to provide a method of increasing the hatch rate of fertile turkey eggs by providing them with free pyridoxine during the incubation period without adversely affecting embryonic survival.

Other objects and advantages of this invention will become obvious from the ensuing description.

DETAILED DESCRIPTION OF THE INVENTION

The pyridoxine composition useful in this invention comprises exogenous pyridoxine dissolved in an inert liquid carrier. For purposes of this invention, the term "pyridoxine" is defined as a substituted pyridine having the structural formula

Pyridoxine, also known as vitamin $B_6$, is available from synthetic sources. It is most commonly produced as the hydrochloride, but other soluble pharmacological salts are also envisioned for use herein. The term "exogenous," as used herein, is meant to refer to pyridoxine produced externally from the egg.

The liquid carrier may be any inert liquid, such as water or isotonic saline solution, that is physiologically compatible with the egg tissue and developing embryo.

An "effective amount" of pyridoxine injected into each egg is defined as that amount which is nontoxic but effective to provide sufficient pyridoxine for survival of the embryo. Amounts in the range of about 200-1,000 $\mu$g pyridoxine per egg, and especially about 600 $\mu$g per egg are preferred. To avoid infecting the egg contents with undesirable pathogens, care must be exercised to assure that the pyridoxine and liquid carrier are sterile and free of pyrogens (bacterial toxins). As a precautionary measure, it is preferred that sterilization and bottling of the pyridoxine be performed under strict aseptic conditions.

The specific mechanism of the injection is not critical provided that it does not unduly damage the shell and underlying shell membranes. It is important to avoid the formation of hairline cracks in the shell and disruption in the physiological functioning of the maternal egg package. Prior to injection, a pilot hole or cavity may be formed through the shell in any suitable manner which will not crack the shell. A 21- to 28-gauge sterile needle locked to a sterile hypodermic syringe is suitable for the purpose. The needle should pierce the shell 3-5 mm on the shell end of the egg or 6-8 mm on the large end. Known and commercially used automatic injectors may also be used provided that stated parameters of caution are maintained. Following injection, the shell may be sealed with paraffin, a fast-drying cement, or other suitable sealant.

For optimum protection of the embryo and to avoid upsetting the physiological stability of the egg, the pyridoxine solution should be injected into the interior of the eggs in a manner which allows the least amount of intrusion without compromising desired results. Underlying shell membranes consist of an outer egg membrane which is directly adjacent to the interior surface of the shell and an inner egg membrane which underlies the outer membrane and surrounds the albumen of the egg. Preferably, the pyridoxine is injected over the inner egg membrane; that is, between the outer and inner egg membranes. The injection is usually made along the longitudinal axis through either the large or small end of the egg shell. The most preferred site is into the air cell enclosed within the outer and inner shell membranes at the large end of the shell.

In accordance with the invention, eggs may be injected any time before depletion of the natural supply of pyridoxine necessary for normal development of the embryo. Preferably, the time for injection of the pyridoxine is at about 25 days of incubation. Advantages of injection on about day 25 are twofold: (1) in a commercial hatchery, eggs are normally transferred from incubation chambers to the hatchers at 25 days and are therefore conveniently available for injection, and (2) embryo failure is highest after 25 days of incubation.

The following examples are intended only to further illustrate the invention and are not intended to limit the scope of the invention which is defined by the claims.

EXAMPLE 1

Preparation of Pyridoxine Solution

Exogenous pyridoxine hydrochloride (USP-FCC, Hoffmann-La Roche, Inc., Nutley, N.J.), 3 g, was dissolved in 1 l of pyrogen-free saline solution (Abbott Laboratories, North Chicago, Ill.). The solution was passed through 0.2-μm filters into empty sterile evacuated bottles (Abbott Laboratories, supra). The bottles were placed in amber bags (Associated Bag Co., Milwaukee, Wis.) to protect the solution from ultraviolet light. If evacuated bottles are not used, the headspace over the solution is filled with nitrogen after passing through a 0.2-μm filter unit, 50 mm (Millipore Products Division, Molsheim, France). The sterilization and solution bottling functions were done under strict sanitized conditions in a dn-class 100 clean room environment with filtered HEPA (high efficiency particulate air), acceptably used to prepare pharmacological solutions for human use.

EXAMPLE 2

Manual Injection of Eggs

Fertile eggs (900) were obtained from a single flock of 240 Nicholas Large White turkey hens for three separate laboratory trials at 8 wks, 12 wks, and 15 wks of egg production. For each trial, a total of 300 eggs were set: 100 for injection with 600 μg exogenous pyridoxine (0.2 ml of the solution described in Example 1), 100 for injection with 0.2 ml saline solution (the carrier for the pyridoxine), and 100 were not injected. At 17 days of incubation, injection through the large end of each egg was performed as follows: The shell area surrounding the injection site was swabbed with 2% iodine tincture. A slight indentation was made in the swabbed area, using a small sharp steel punch that was flamed before contacting the shell. The force used on the punch was slight, to avoid forming hairline cracks in the shell. The punch site exactly accommodated a microfine III, 28-gauge sterile needle that was locked to a 0.5-ml sterile insulin syringe (Becton Dickinson, Inc., Rutherford, N.J.). The needle was carefully inserted through the punch site to a depth of about 6–8 mm, and 0.2 ml of the desired solution was injected over the inner shell membrane. The puncture was sealed with a small drop of fast-drying "Duco Cement" (Devcon Corp., Wood Dale, Ill.) which was lightly layered over the puncture site. The injections were done under a strictly sanitized, clean-room environment with HEPA, and personnel were asceptically equipped for handling the experimental solutions. The data reported in Table I show that pyridoxine injection over the three trials effected in average 4.5% increase in hatchability and that injection with the carrier saline solution had no effect on hatchability.

EXAMPLE 3

Automatic Injection of Eggs

Fertile eggs were obtained from two flocks (6,000 hens each) of Nicholas Large White turkeys for three separate field trials at 16 wks, 20 wks, and 24 wks of egg production. For each trial, 544 eggs were set for injection with exogenous pyridoxine (at the same level as in Example 2) and another 544 eggs were not injected. At 25 days of incubation, injection was performed as follows: The eggs were dipped in antiseptic solution and injected at the small end with 0.2 ml of exogenous pyridoxine solution (supra) using an automatic egg injector. The injection needles were approximately 21 gauge (flat ends), and the eggs were pierced to a depth of approximately 3–5 mm. After injection, the needle sites were sealed with wax, and incubation was resumed.

The data was analyzed as a two-factor block analysis of variance. Trial and treatment were the factors, and flock was the block. The main effects, trial and treatment, were each significant ($P<0.0021$); trial x treatment was not. In all trials, pyridoxine-injected eggs gave significantly higher ($P<0.002$) hatchability over uninjected eggs (Table II). There was a 4.6% increase in hatchability of injected eggs, compared to the control for the six trials combined using the two flocks. The results of the individual trials for flock 1 and flock 2 (6,000 hens each) are reported in Table II. Statistical significance of the six trials combined is reported in Table III. The results in Examples 2 and 3 demonstrate that it made no difference whether the eggs were injected at the large or the small end, nor whether they were injected at 17 or 25 days incubation time.

It is understood that the foregoing detailed description is given merely by way of illustration and that modification and variations may be made therein without departing from the spirit and scope of the invention.

TABLE I

| | Results of Manual Injection | | | |
| | Hatchability (%) | | | |
| Treatment | At 8 wk production (Trial 1) | At 12 wk production (Trial 2) | At 15 wk production (Trial 3) | Pooled means |
| --- | --- | --- | --- | --- |
| Pyridoxine-injected | 93.8 | 84.0 | 89.8 | 89.2[a] |
| Saline-injected | 88.0 | 81.0 | 85.0 | 84.7[b] |
| Not injected | 89.7 | 81.0 | 83.8 | 84.8[b] |

[a,b]Values with different superscripts are significantly different (P <0.05).

TABLE II

Results of Automatic Injection, Individual Trials

| | Hatchability (%)[1] | | |
| --- | --- | --- | --- |
| | At 16 wk production | At 20 wk production | At 24 wk production |
| Treatment | | | |
| Flock 1 | Trial 1 | Trial 2 | Trial 3 |
| Pyridoxine-injected | 91.4 | 90.6 | 91.1 |
| Not injected | 88.0 | 88.2 | 84.4 |
| Flock 2 | Trial 4 | Trial 5 | Trial 6 |
| Pyridoxine-injected | 88.0 | 87.5 | 89.0 |
| Not injected | 82.1 | 85.8 | 82.5 |

[1]In all trials, pyridoxine-injected eggs gave significantly higher (P <0.002) hatchability over uninjected eggs.

TABLE III

Results of Automatic Injection, Combined Trials

| Treatment | Eggs set[1] (No.) | Hatchability[2] (%) |
| --- | --- | --- |
| Pyridoxine-injected | 3264 | 89.8 |
| Not injected | 3264 | 85.2 |

[1]Eggs set represent six trials from two different turkey flocks (three trials per flock, 544 eggs per treatment in each trial, incubated at 16, 20, and 24 wks of production).
[2]Hatchability was significantly higher (P <0.002) in pyridoxine-injected eggs over noninjected eggs in the six trials.

I claim:

1. A method for increasing the hatch rate of incubated fertile turkey eggs comprising injecting the incubated eggs with an amount of exogenous pyridoxine in the range of about 200–1,000 µg pyridoxine per egg to increase the hatch rate of the eggs, and wherein said eggs are incubated about 25 days before injection.

2. The method of claim 1 wherein said pyridoxine is deposited between the outer and inner shell membranes.

3. The method of claim 1 wherein the site of injection is substantially along the longitudinal axis.

4. The method of claim 3 wherein the site of injection is the air sac at the large end of the egg.

* * * * *

UNITED STATES PATENT AND TRADEMARK OFFICE
CERTIFICATE OF CORRECTION

PATENT NO. : 4,973,595

DATED : November 27, 1990

INVENTOR(S) : Edward J. Robel

It is certified that error appears in the above-identified patent and that said Letters Patent is hereby corrected as shown below:

Column 2, line 6, delete "batch" and insert -- hatch -- ;
Column 2, line 63, delete "shell" and insert --small -- .

Signed and Sealed this

Eleventh Day of August, 1992

Attest:

DOUGLAS B. COMER

*Attesting Officer*    *Acting Commissioner of Patents and Trademarks*